United States Patent [19]

Ikesu et al.

[11] Patent Number: 4,914,013
[45] Date of Patent: Apr. 3, 1990

[54] SILVER HALIDE LIGHT-SENSITIVE COLOR PHOTOGRAPHIC MATERIAL

[75] Inventors: Satoru Ikesu; Noboru Mizukura, both of Hino, Japan

[73] Assignee: Konica Corporation, Tokyo, Japan

[21] Appl. No.: 317,935

[22] Filed: Mar. 2, 1989

[30] Foreign Application Priority Data

Mar. 25, 1988 [JP] Japan .................... 63-71264

[51] Int. Cl.$^4$ ............................................... G03C 7/38
[52] U.S. Cl. ...................................... 430/555; 430/554
[58] Field of Search .................. 430/543, 554, 555

[56] References Cited

U.S. PATENT DOCUMENTS

| | | | |
|---|---|---|---|
| 4,363,873 | 12/1982 | Boon et al. ........................ | 430/554 |
| 4,609,620 | 9/1986 | Postle et al. ...................... | 430/554 |
| 4,628,592 | 5/1981 | Tschopp .......................... | 430/554 |
| 4,696,893 | 9/1987 | Umemoto et al. ................ | 430/554 |
| 4,745,050 | 5/1988 | Seto et al. ....................... | 430/555 |

*Primary Examiner*—Richard L. Schilling
*Attorney, Agent, or Firm*—Jordan B. Bierman

[57] ABSTRACT

A silver halide color photographic light-sensitive material is disclosed, which contains a magenta coupler having a specific ballast group. The light-sensitive material is improved in solubility in an organic solvent, dispersibility and stability of dispersion in a silver halide emulsion. The coupler is represented by the following Formula M-1;

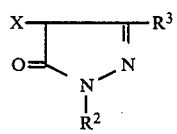

Formula M-I wherein $R^2$ and $R^3$ are each a substituent provided that and at least one of which has a group represented by the following Formula I; and X is a hydrogen atom or a group capable of being split off upon reaction with the oxidation produce of a color developing agent;

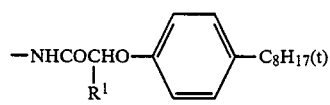

Formula I wherein $R^1$ is a hydrogen atom or a normal or branched alkyl group having 1 to 20 carbon atoms.

8 Claims, No Drawings

SILVER HALIDE LIGHT-SENSITIVE COLOR PHOTOGRAPHIC MATERIAL

FIELD OF THE INVENTION

The present invention relates to a silver halide light-sensitive color photographic material, and more particularly to a silver halide light-sensitive color photographic material containing a 5-pyrazolone-type magenta coupler having a specific ballasting group.

BACKGROUND OF THE INVENTION

In silver halide light-sensitive color photographic materials (hereinafter may sometimes be called color light-sensitive materials(s)), as the magenta coupler for forming a magenta dye, 5-pyrazolone compounds have been widely used to date. A useful method for adding the magenta coupler to a photographic emulsion comprises introducing a oleophilic ballasting group into the coupler molecule, dissolving the ballasting group-introduced coupler into a high-boiling organic solvent, and then emulsifiedly dispersing the coupler solution into a hydrophilic colloid such as gelatin.

The essential nature required for the coupler is that the coupler shall have a large solubility in high-boiling organic solvents;

have satisfactory dispersibility and dispersing stability and be hardly deposited in a silver halide emulsion;

be capable of forming a dye image which is so excellent in the spectral absorption characteristic as to provide a good tone, clear color image in a wide color reproducing region range;

provide a dye image which is resistant against light, heat and moisture; and be producible at a good reproducibility from inexpensive raw materials in accordance with a simple synthesis method and yet at a high yield.

The ballasting group plays an important role for these characteristics, and includes those specific ballasting groups as described in Japanese Patent Examined Publication Nos. 3660/1969, 25655/1973, 25932/1973, 25934/1973, 16057/1974 and 40804/1976; Japanese Patent Publication Open to Public Inspection (hereinafter referred to as Japanese Patent O.P.I. Publication) Nos. 4481/1972, 8228/1974, 19435/1975, 126831/1976, 86333/1977, 30126/1981, 146251/1982, 42045/1983, 177557/1984 and 24547/1985; and U.S. Pat. Nos. 2,908,573, 2,920,961 and 3,227,544.

However, these ballasting groups are still insufficient to satisfy the above-mentioned characteristics. For example, as the ballasting group, the Japanese Patent Examined Publication No. 25934/1973 discloses 2-(3-dodecyloxyphenoxy)butylamido group (1); the Japanese Patent O.P.I. Publication No. 4481/1972 discloses 4,6-dicyclopentyl-3-methylphenoxy group (2); the Japanese Patent Examined Publication No. 3660/1969 discloses 2,4-di-sec-amylphenoxyacetamido group (3); the Japanese Patent O.P.I. Publication No. 86333/1977 discloses 4-nonylphenoxycarbonylethylamido group (4); the Japanese Patent O.P.I. Publication No. 177557/1984 discloses sulfamoylphenylenesulfonyl group (5); and the Japanese Patent Examined Publication No. 40804/1976 discloses 4-nonylphenoxyacetamido group (6). Those magenta couplers obtained by introducing the groups (1), (2), (4) and (6) out of the above-mentioned ballasting groups into 5-pyrazolone compounds all show excellent solubility in high-boiling organic solvents, but in the case of (1) and (4), the formed dyes' spectral absorption range is too broad, while in the case of (2) and (6), it is difficult to refine the produced couplers therefrom.

In the case of (3), the obtained coupler's solubility in high-boiling organic solvents is not deemed sufficient, while in (5), the obtained coupler is improved on its color formability but lacks solubility in high-boiling organic solvents.

Thus, development of such ballasting groups as to meet all the essential nature required for the foregoing couplers has been demanded.

SUMMARY OF THE INVENTION

The present invention has been made in light of the above-mentioned circumstances.

It is a first object of the present invention to provide a color light-sensitive material which contains a magenta coupler having a high solubility in organic solvents (high-boiling organic solvent and low-boiling organic solvent) and satisfactory dispersibility and dispersing stability in a silver halide emulsion.

It is a second object of the present invention to provide a color light-sensitive material which contains a magenta coupler capable of forming a magenta dye having a satisfactory spectral absorption characteristic and which has a high sensitivity and an excellent gradation.

It is a third object of the present invention to provide a color light-sensitive material which is capable of forming a dye image excellent in the fastness against light, heat and moisture.

It is a fourth object of the present invention to provide a color light-sensitive material which contains a magenta coupler that can be well reproducibly obtained at a high yield from inexpensive raw materials in accordance with a simple synthesis method.

The above objects of the present invention are accomplished by a silver halide color photographic light-sensitive material comprising a support having thereon at least one silver halide emulsion layer containing a 5-pyrazolone-type magenta coupler represented by the following Formula M-1:

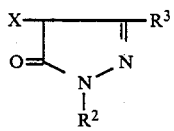

Formula M-1 wherein $R^2$ and $R^3$ are each a substituent, provided that at least one of said substituents has a ballasting group represented by the following Formula I; and X is a hydrogen atom or a group capable of being split off upon reaction with the oxidation product of a color developing agent,

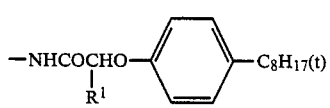

Formula I wherein $R^1$ is a hydrogen atom or a normal or branched alkyl group having 1 to 20 carbon atoms.

DETAILED DESCRIPTION OF THE INVENTION

The 5-pyrazolone-type magenta coupler to be used in this invention is represented by the following Formula M-I:

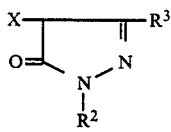
Formula M-I wherein $R^2$ and $R^3$ each represents a substituent, and at least one of the $R^2$ and $R^3$ is a group having as its partial structure a group having Formula I; and X represents a hydrogen atom or a group capable of splitting off upon the reaction with the oxidation product of color developing agent.

The magenta coupler having Formula M-I includes those in the form of bis-type or polymer couplers.

To be concrete, the $R^2$ represents an aryl group including substituted one, and preferably a phenyl group having a substituent. Preferred examples of the substituent include a halogen atom such as fluorine, chlorine, bromine; an alkyl group such as methyl, ethyl, butyl, etc.; an alkoxy group such as methoxy, ethoxy, etc.; an aryloxy group such as phenoxy, naphthoxy, etc.; an acylamino group such as α-(2,4-di-t-amylphenoxy)-butylamido, benzamido, etc.; a sulfonylamino group such as hexadecanesulfonamido, benzenesulfonamido, etc.; a sulfamoyl group such as methylsulfamoyl, phenylsulfamoyl, etc.; a carbamoyl group such as methylcarbamoyl, phenylcarbamoyl, etc.; a sulfonyl group such as methylsulfonyl, dodecylsulfonyl, benzenesulfonyl, etc.; an acyloxy group, an ester group, a carboxyl group, a sulfo group, a cyano group, a nitro group, and the like.

The $R^3$ represents an anilino group such as anilino, 2-chloroanilino, 2,4-dichloroanilino, 4-cyanoanilino, 2,4-dichloro-5-methoxyanilino, etc.; an acylamino group such as tetradecaneamido, α-(3-pentadecylphenoxy)butylamido, benzamido, 3-acetamidobenzamido, 3-benzenesulfonamidobenzamido, etc.; a ureido group such as methylureido, phenylureido, etc.; or a carbamoyl group such as tetradecylcarbamoyl, phenylcarbamoyl, etc.

The group capable of being split off upon the reaction with the oxidation product of a color developing agent is, for example, a halogen atom such as chlorine, bromine, fluorine, etc., or a group such as alkoxy, aryloxy, heterocyclic oxy, acyloxy, sulfonyloxy, alkoxycarbonyloxy, aryloxycarbonyl, alkyloxalyloxy, alkoxyoxalyloxy, alkylthio, arylthio, heterocyclic thio, alkyloxythiocarbonylthio, acylamino, sulfonamido, nitrogen-containing heterocyclic group linked with a nitrogen atom, alkyloxycarbonylamino, aryloxycarbonylamino, or the like.

In Formula M-I, at least one of the $R^2$ and $R^3$ has as its partial structure an α-(4-t-octylphenoxy)alkaneamido group represented by Formula I.

In Formula I, the straight-chain or branched-chain alkyl group having from 1 to 20 carbon atoms, represented by the $R^1$, includes methyl, ethyl, i-propyl, butyl, t-butyl, hexyl, octyl, dodecyl, palmityl, octadecyl and the like groups.

The $R^1$ is preferably a hydrogen atom or an alkyl group having from 1 to 12 carbon atoms.

The following are typical examples of the magenta coupler having Formula M-I of this invention (hereinafter referred to as the magenta coupler of this invention), but the invention is not limited to and by the examples.

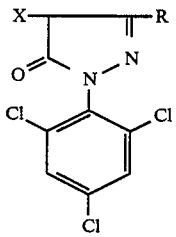

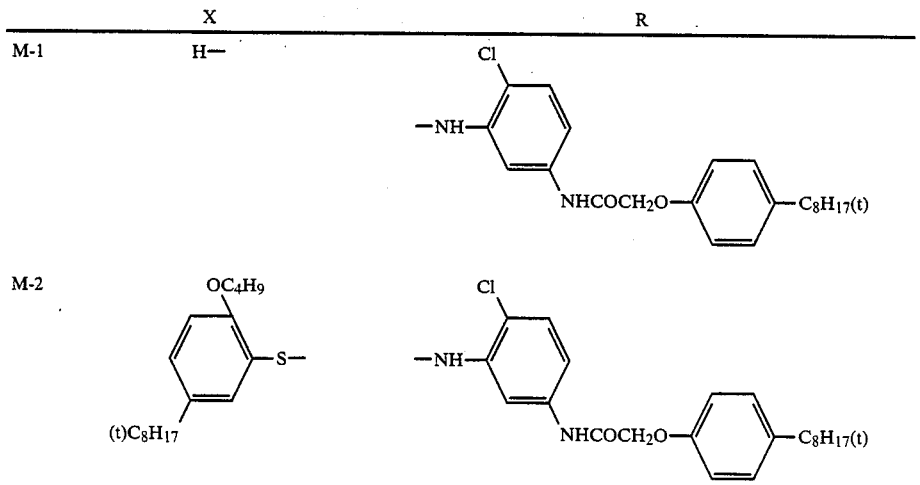

-continued
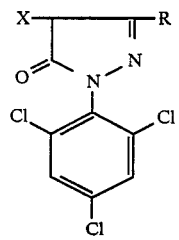
| | X | R |
|---|---|---|
| M-3 | H— | —NH—(4-Cl, 3-position)C₆H₃—NHCOCH(CH₃)O—C₆H₄—C₈H₁₇(t) |
| M-4 | pyrazol-1-yl (N–N=CH–CH=CH) | —NH—(4-OCH₃)C₆H₃—NHCOCH(CH₃)O—C₆H₄—C₈H₁₇(t) |
| M-5 | H— | —NH—(4-Cl)C₆H₃—NHCOCH(C₂H₅)O—C₆H₄—C₈H₁₇(t) |
| M-6 | H— | —NH—(4-OCH₃)C₆H₃—NHCOCH(C₂H₅)O—C₆H₄—C₈H₁₇(t) |
| M-7 | 1-phenyl-1H-tetrazol-5-ylthio | —NH—(4-Cl)C₆H₃—NHCOCH(C₂H₅)O—C₆H₄—C₈H₁₇(t) |
| M-8 | H— | —NH—(4-Cl)C₆H₃—NHCOCH(C₄H₉)O—C₆H₄—C₈H₁₇(t) |

-continued
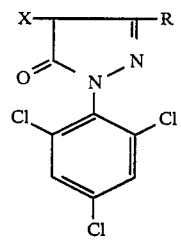
| | X | R |
|---|---|---|
| M-9 | 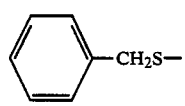 | 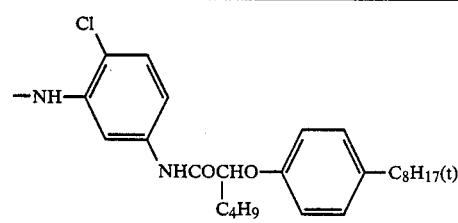 |
| M-10 | H— | 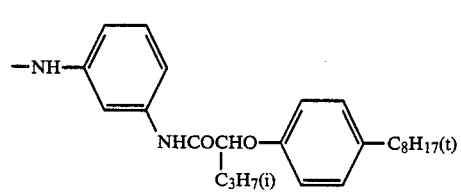 |
| M-11 | $CF_3CONH-$ | 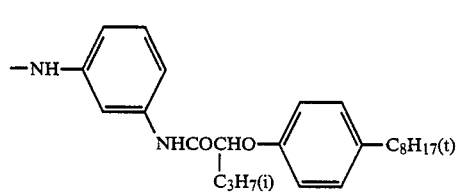 |
| M-12 | H— | 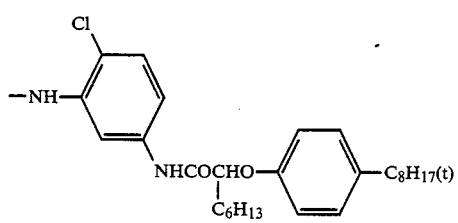 |
| M-13 | H— | 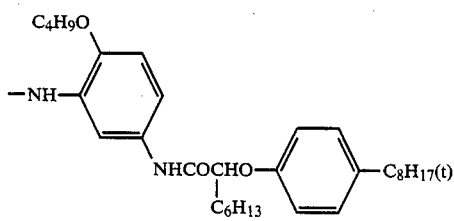 |
| M-14 | 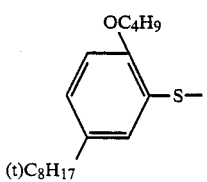 | 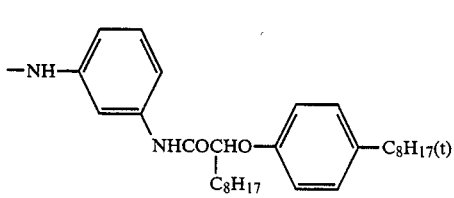 |

-continued
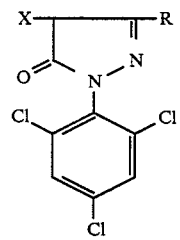
| | X | R |
|---|---|---|
| M-15 | H— | —NH—(4-Cl-phenyl with 3-NHCOCH(C₁₂H₂₅)O-C₆H₄-C₈H₁₇(t)) |
| M-16 | H— | —NHCOCH₂O—C₆H₄—C₈H₁₇(t) |
| M-17 | H— | —NHCOCH(C₂H₅)O—C₆H₄—C₈H₁₇(t) |
| M-18 | H— | —NHCOCH(C₄H₉)O—C₆H₄—C₈H₁₇(t) |
| M-19 | 2-OC₄H₉-4-(t)C₈H₁₇-phenyl-S— | —NHCOCH(C₂H₅)O—C₆H₄—C₈H₁₇(t) |
| M-20 | H— | —NHCO—(3-NHCOCH₂O-C₆H₄-C₈H₁₇(t))-phenyl |
| M-21 | H— | —NHCO—(3-NHCOCH(C₂H₅)O-C₆H₄-C₈H₁₇(t))-phenyl |
| M-22 | H— | —NHCO—(4-Cl-3-NHCOCH(C₄H₉)O-C₆H₄-C₈H₁₇(t))-phenyl |

-continued

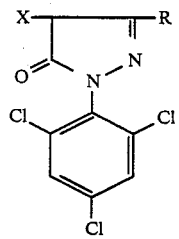

| | X | R |
|---|---|---|
| M-23 | 2-OC₄H₉, 4-(t)C₈H₁₇-phenyl-S— | —NHCO-(3-{NHCOCH(C₂H₅)O-C₆H₄-4-C₈H₁₇(t)}-C₆H₄) |
| M-24 | 2-O(CH₂)₂O(CH₂)₂OCH₃, 4-(t)C₈H₁₇-phenyl-S— | —NHCO-(3-{NHCOCH₂O-C₆H₄-4-C₈H₁₇(t)}-C₆H₄) |
| M-25 | 2-O(CH₂)₂O(CH₂)₂OCH₃, 4-(t)C₈H₁₇-phenyl-S— | —NH-(2-Cl-5-{NHCOCH(C₂H₅)O-C₆H₄-4-C₈H₁₇(t)}-C₆H₃) |
| M-26 | pyrazol-1-yl | —NHCO-(3-{NHCOCH(C₄H₉)O-C₆H₄-4-C₈H₁₇(t)}-C₆H₄) |
| M-27 | H— | —NHCO-(3-{NHCOCH(C₁₂H₂₅)O-C₆H₄-4-C₈H₁₇(t)}-C₆H₄) |
| M-28 | H— | —NHCONH-(3-{NHCOCH₂O-C₆H₄-4-C₈H₁₇(t)}-C₆H₄) |
| M-29 | CH₃COO— | —NHCONH-(3-{NHCOCH₂O-C₆H₄-4-C₈H₁₇(t)}-C₆H₄) |

| | X | R |
|---|---|---|
| M-30 | | 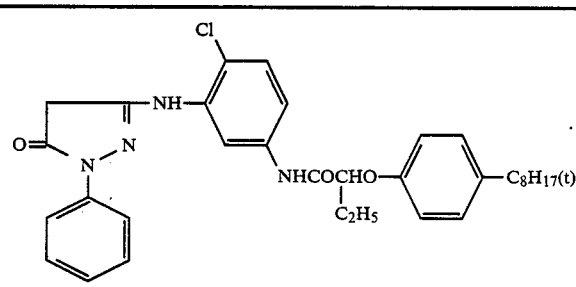 |
| M-31 | | 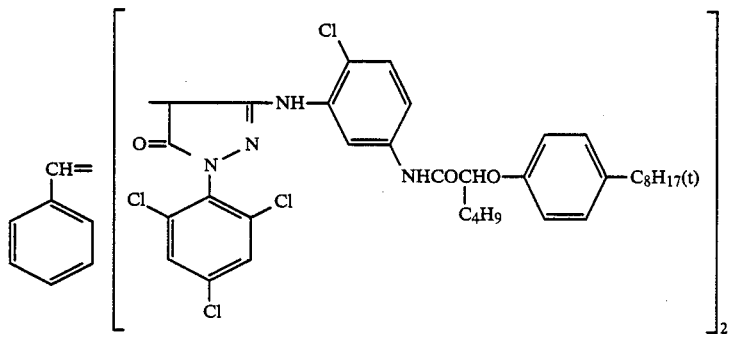 |
| M-32 | | 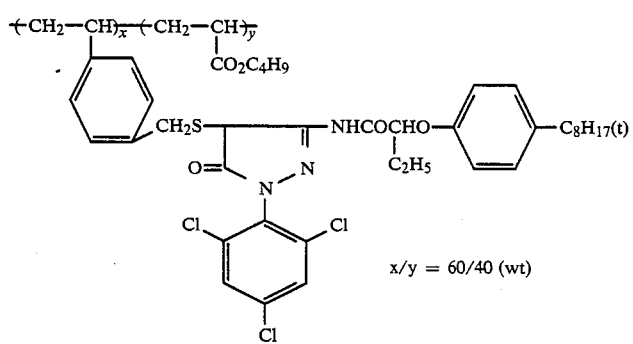 |
| M-33 | | 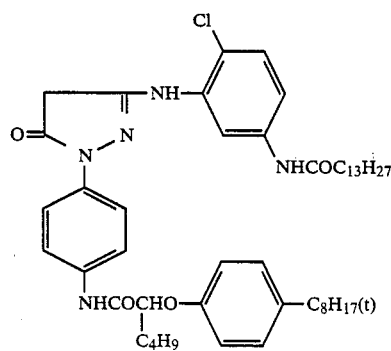 |

-continued

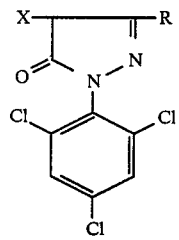

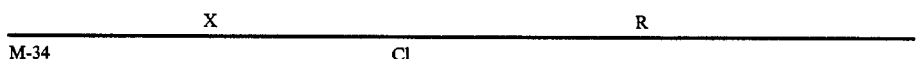

M-34 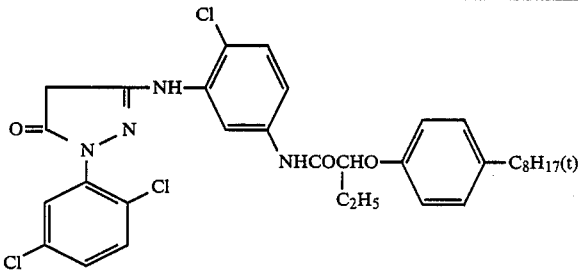

M-35

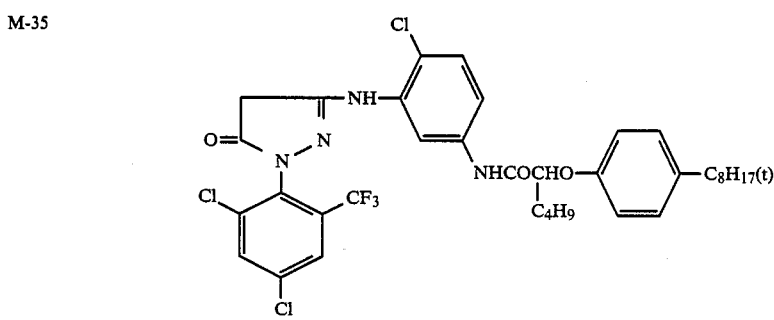

M-36

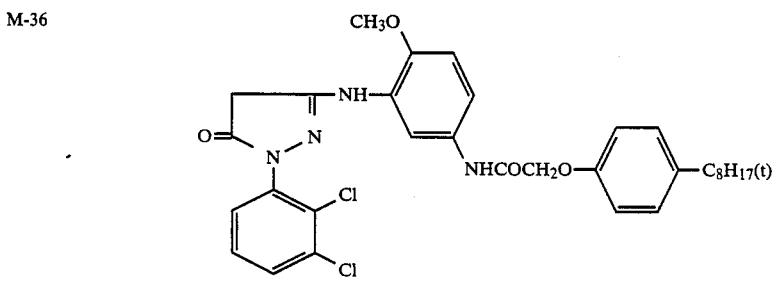

M-37

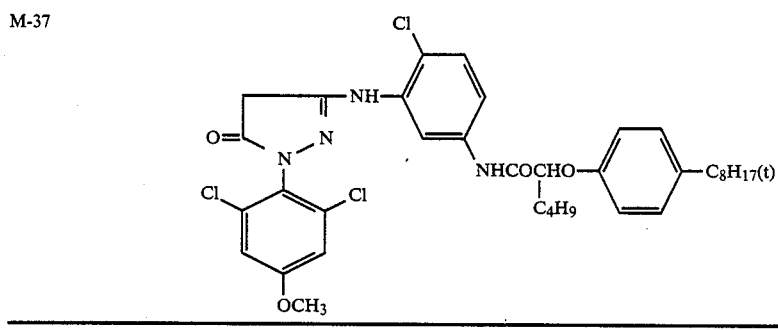

The ballasting group of Formula I can be easily synthesized in the manner, as described in Japanese Patent Examined Publication Nos. 25934/1973 and 40804/1976, that the ethyl α-(p-t-octylphenoxy)-α-bromoacetate, which has been synthesized from p-t-octylphenol and ethyl α-bromoacetate, is made into an acid chloride, and the acid chloride is then made react with the amino group of 5-pyrazolone.

Typical synthesis examples of the coupler of this invention will now be given below:

SYNTHESIS EXAMPLE 1

(Synthesis of Exemplified Compound M-1)

Forty point four grams of 1-(2,4,6-trichlorophenyl)-3-(2-chloro-5-aminoanilino)-5-pyrazolone were dissolved into 250 ml of acetonitrile, and to the solution were added 9.4 grams of pyridine. To this mixture, while being refluxed by heating, were dropwise added 28.3 g of 4-t-octylphenoxyacetyl chloride, and the reflux was further continued for another hour. The acetonitrile was distilled off from the reaction liquid under reduced pressure, then 500 ml of water and ethyl acetate were added to the liquid, and then the reaction product was extracted by ethyl acetate. The residuum that has been obtained by distilling off the ethyl acetate phase under reduced pressure was recrystallized from 300 ml of ethanol, whereby 55 g of objective 1-(2,4,6-trichlorophenyl)-3-[2-chloro-5-(4-t-octylphenox-yacetamido)anilino]-5-pyrazolone were obtained. Melting point: 126° to 128° C. The structure was confirmed through the procedures of NMR, IR and MASS.

SYNTHESIS EXAMPLE 2

(Synthesis of Exemplified Compound M-5)

Forty point four grams of 1-(2,4,6-trichlorophenyl)-3-(2-chloro-5-aminoanilino)-5-pyrazolone were suspended in 120 ml of ethyl acetate, and to this mixture were added 40 ml of an aqueous solution containing 9.62 g of sodium acetate. At room temperature, 31.1 g of 2-(4-t-octylphenoxy)-butyric acid chloride were added dropwise to the liquid, and the mixture was stirred for another hour at room temperature. The organic phase was separated from the reaction liquid, and the solvent was distilled off under reduced pressure. The residuum was recrystallized from 300 ml of ethanol, whereby 58 g of objective 1-(2,4,6-trichlorophenyl)-3-[2-chloro-5-{2-(4-t-octylphenoxy)butaneamido}anilino]-5-pyrazolone were obtained. Melting point: 163° to 165° C. The structure was confirmed through the procedures of NMR, IR and MASS.

Those methods and techniques which are used for ordinary magenta dye-forming couplers may be applied as well to the magenta coupler of this invention. Typically, the magenta coupler of this invention is incorporated into a silver halide emulsion, and this emulsion is coated on a support to thereby form a color light-sensitive material of this invention.

The color light-sensitive material of this invention is, for example, a color negative or positive film, color photographic paper, or the like.

The light-sensitive material of this invention, including the color photographic paper, may be for either monocolor use or multicolor use. Where the light-sensitive material is a multicolor light-sensitive material, the magenta coupler of this invention is to be incorporated into a green-sensitive silver halide emulsion layer. The multicolor light-sensitive material has three dye image-forming components sensitive to the relevant three primaries' regions, respectively, of the spectrum. Each component may be comprised of a single emulsion layer or a plurality of emulsion layers having sensitivity to a certain region of the spectrum. All the component layers of the light-sensitive material, including the image-forming component layers, may be arranged in any discretional order as well-known to those skilled in the art. A typical multicolor light-sensitive material comprises a support having thereon a cyan dye image-forming component comprising at least one red-sensitive silver halide emulsion layer containing at least one cyan coupler, a magenta dye image-forming component comprising at least one green-sensitive silver halide emulsion layer containing at least one magenta coupler (at least one of magenta couplers is the magenta coupler of this invention), and a yellow dye image-forming component comprising at least one blue-sensitive silver halide emulsion layer containing at least one yellow coupler. The light-sensitive material may have additional layers such as, for example, filter layers, intermediate layers, a protective layer, a subbing layer, and the like.

Incorporation of the magenta coupler of this invention into an emulsion may be performed in accordance with any of conventionally known methods. For example, a single magenta coupler or combined magenta couplers of this invention are dissolved into a single high-boiling organic solvent having a boiling point of not less than 175° C., such as tricresyl phosphate, dibutyl phthalate or the like, or a single low-boiling organic solvent such as ethyl acetate, butyl propionate or the like, or, if necessary, a mixture of these high-boiling and low-boiling solvents, and the magenta coupler solution is then mixed with an aqueous gelatin solution containing a surface active agent. The mixture liquid, after being emulsified by means of a high-speed rotary mixer or a colloid mill, is subsequently added to a silver halide emulsion, whereby a silver halide emulsion for use in this invention can be prepared.

The coupler of this invention may be used in the amount range of normally from $7 \times 10^{-2}$ to $7 \times 10^{-1}$ mole, and preferably from $1 \times 10^{-1}$ to $4 \times 10^{-1}$ mole per mole of silver halide.

The coupler of this invention may also be used in combination with different other couplers.

The silver halide composition suitably usable in this invention include silver chloride, silver chlorobromide and silver chloroiodobromide, and may also be a mixture in combination of silver chloride with silver bromide, and the like.

The silver halide emulsion is chemically sensitized in usual manner, and may also be optically sensitized to a desired wavelength region.

To the silver halide emulsion may be added a compound which is known as an antifoggant or stabilizer to those skilled in the art for the purpose of the antifogging of and/or keeping stable the photographic characteristics of the lightsensitive material during its manufacturing process, during its storage, or during its photographic processing.

The color light-sensitive material of this invention may use those agents usually applicable to ordinary light-sensitive materials, such as anti-color-stain agents, dye image stabilizers, ultraviolet absorbing agents, antistatic agents, matting agents, surface active agents, and the like.

For these agents reference can be made to, e.g., Research Disclosure Vol. 176, pp. 22–31 (Dec. 1978).

The color light-sensitive material of this invention forms an image when processed according to the color development precedure known to those skilled in the art.

The color light-sensitive material of this invention may contain in its hydrophilic colloid layer a color developing agent as it is or in the form of a precursor in order to be processed in an alkaline activator bath.

The color light-sensitive material of this invention, after its color development, is processed in bleaching and fixing baths. The bleaching and mixing may take place simultaneously.

The fixing process may be usually followed by a washing process. A stabilization process may substitute for the washing process, or both may be used in combination.

The magenta coupler of this invention is used in combination with yellow and cyan couplers in order to prepare a multicolor light-sensitive material.

As the yellow coupler, an open-chain or heterocyclic ketomethylene compound may be used, but it is preferable to use an α-benzoylacetanilide-type compound in respect of giving a higher color density and an α-pivaloylacetanilide-type compound in respect of the fastness of its formed dye, particularly its resistance to light.

Particularly suitably usable yellow couplers are those compounds having the following Formula Y-I:

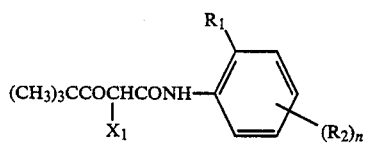

Formula Y-I wherein $R_1$ represents a halogen atom, an alkoxy group or an alkyl group; $R_2$ represents a group capable of being a substituent to the benzene ring; n is an integer of 1 or 2, provided that when n is 2, the two $R_2$s may be either the same or different; and $X_1$ is a group capable of being split off upon reaction with the oxidation product of a color developing agent. Preferred among the substituents represented by the $R_1$ are halogen atoms and lower alkoxy groups, and particularly preferred one is a halogen atom such as fluorine, chlorine, bromine, or the like. The substituents represented by the $R_2$, although not particularly restricted, are preferably $R'_2CONH—$, $R'_2SO_2NH—$ and $R'_2OCONH—$ (wherein $R'_2$ is an alkyl group including substituted one), and above all, the $R'_2CONH—$ is particularly preferred. Preferred as the substituent represented by the $X_1$ are aryloxy group, heterocycloxy group and

(wherein Z is a group of atoms selected from the class consisting of carbon, oxygen, nitrogen and sulfur, necessary to form a 5- or 6-member ring together with the nitrogen atom), and particularly the aryloxy group and the

are preferred.

The following are typical examples of the yellow coupler.

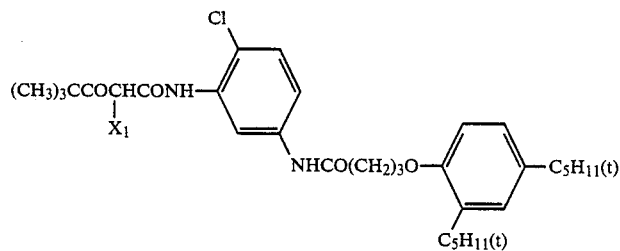

| | $X_1$ |
|---|---|
| Y-1 | 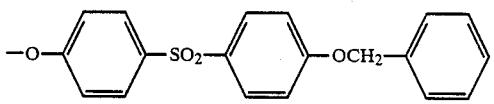 |
| Y-2 | 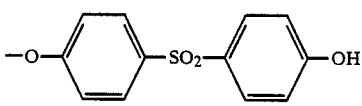 |
| Y-3 | 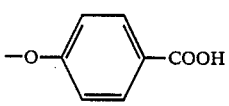 |
| Y-4 | 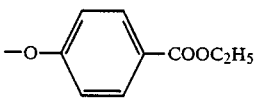 |

-continued
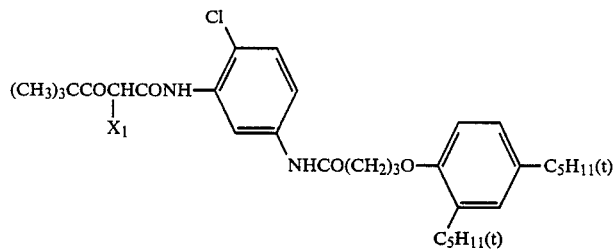
| | $X_1$ |
|---|---|
| Y-5 | 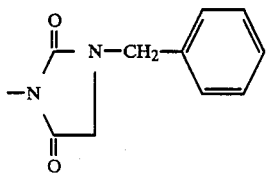 |
| Y-6 | 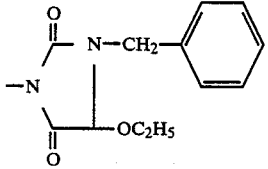 |
| Y-7 | 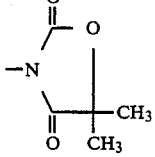 |
| Y-8 | 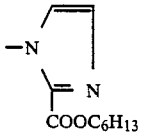 |
Y-9
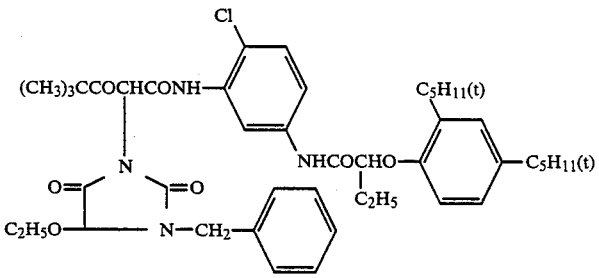
Y-10
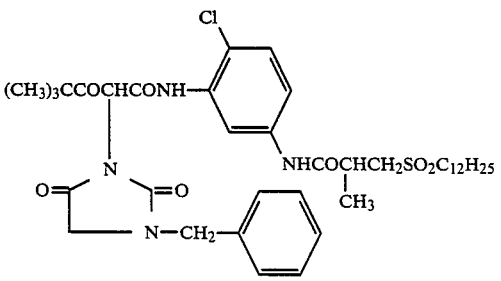

-continued
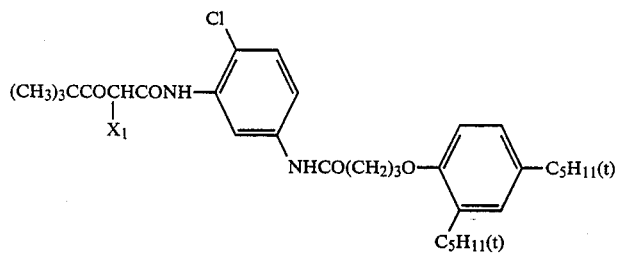
| X₁ | |
|---|---|
| Y-11 | 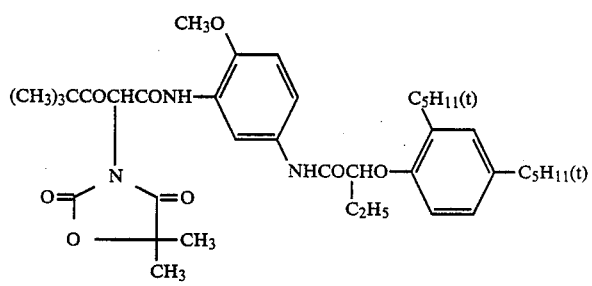 |
| Y-12 | 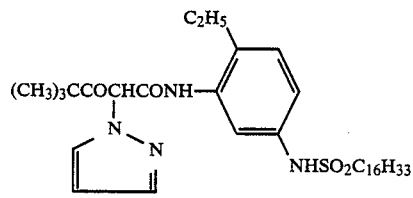 |
| Y-13 | 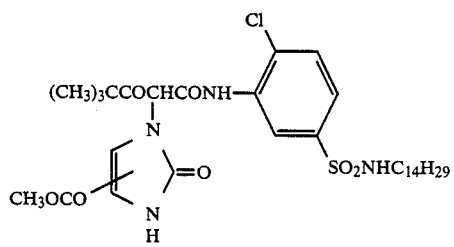 |
| Y-14 | 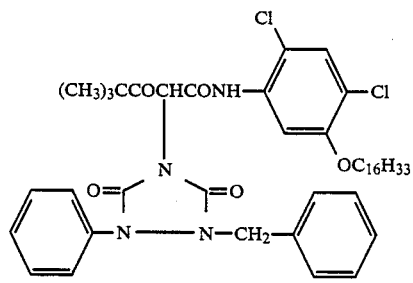 |
| Y-15 | 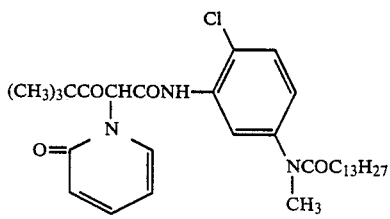 |

-continued
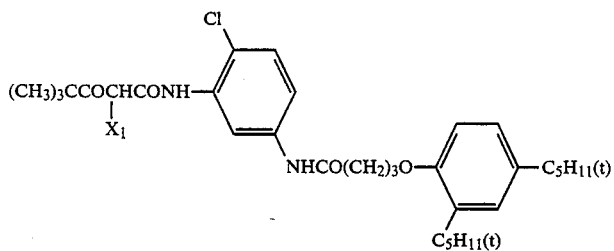
| $X_1$ | |
|---|---|
| Y-16 | 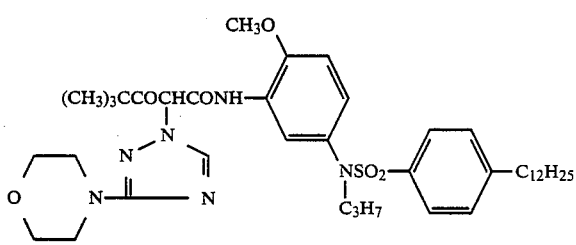 |
| Y-17 | 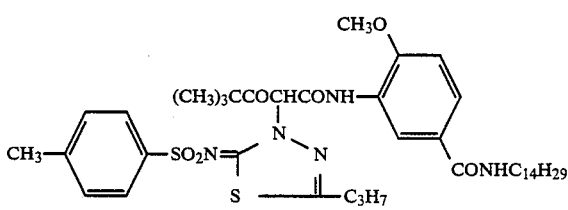 |
| Y-18 | 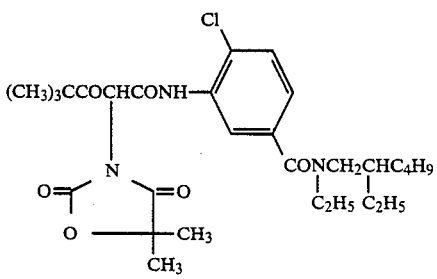 |
| Y-19 | 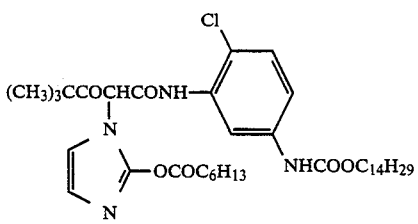 |
| Y-20 | 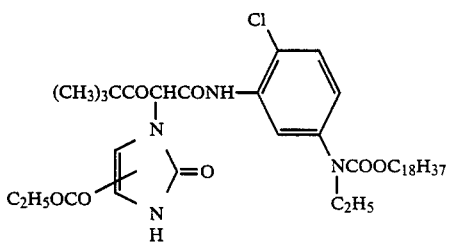 |

-continued

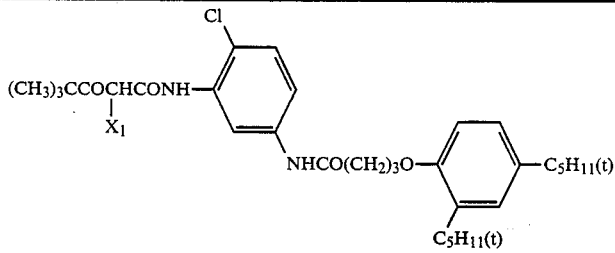

| | $X_1$ |
|---|---|
| Y-21 | 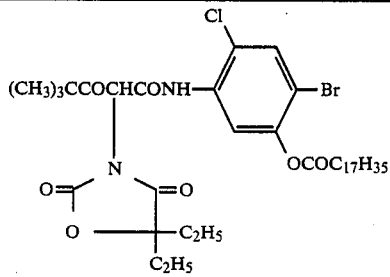 |
| Y-22 | 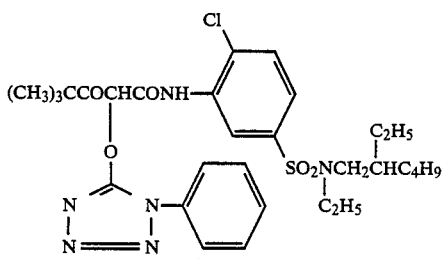 |
| Y-23 | 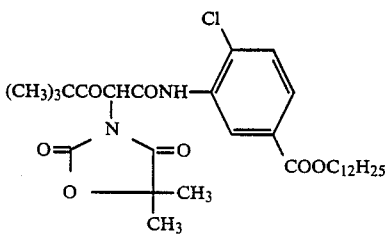 |
| Y-24 | 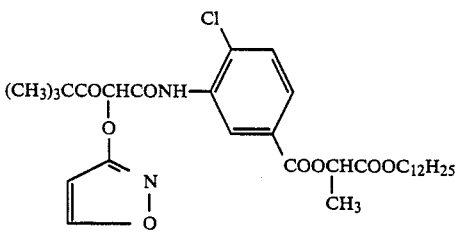 |
| Y-25 | 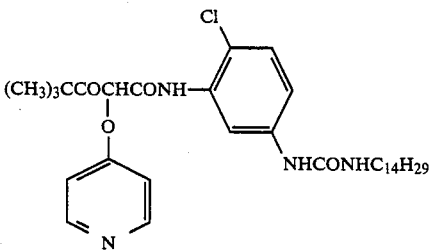 |

The magenta coupler of this invention is one improved on its solubility, dispersing stability, spectral absorption characteristic and resistance to light. Some of the abovementioned yellow couplers, when used in combination with the magenta coupler of this invention, may be further improved on their characteristics. The reason for the improvement is not certain, but is probably because some component that has split off the yellow coupler exhibits its effect.

As the cyan coupler, naphthol-type and phenol-type cyan couplers are used. Particularly suitable cyan couplers are those compounds having the following Formula C-I and Formula C-II:

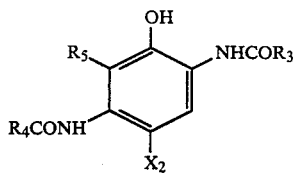

Formula C-I

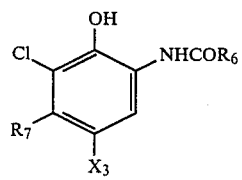

Formula C-II wherein $R_3$ represents an alkyl group, a cycloalkyl group, an aryl group, a heterocyclic group, an alkoxy group, an aryloxy group, an alkylamino group or an arylamino group; $R_4$ represents an alkyl group, a cycloalkyl group or an aryl group; $R_5$ is a hydrogen atom, a halogen atom, an alkyl group or an alkoxy group, provided that the $R_4$ and $R_5$ may combine with each other to form a 5- or 6-member ring; and $X_2$ is a hydrogen atom or a group capable of being split off upon reaction with the oxidation product of a color developing agent.

wherein $R_6$ represents an alkyl group or an aryl group; $R_7$ represents an alkyl or alkoxy group each having from 1 to 5 carbon atoms; and $X_3$ is a hydrogen atom or a group capable of being split off upon the reaction with the oxidation product of a color developing agent, provided that the $R_7$ and $X_3$ may combine with each other to form a 5- or 6-member ring.

In Formula C-I, preferred one of the substituents represented by the $R_3$ is the aryl group, particularly an aryl group substituted by a halogen atom, alkylsulfonamido group, alkoxy group, cyano group or the like. The substituent represented by the $R_4$ is preferably an aryloxy group, and particularly preferably a ballasting group composed of a branched alkyl group substituted by an alkoxy group. The $X_2$ is preferably a halogen atom, particularly a chlorine atom.

In Formula C-II, preferred among the substituents represented by the $R_6$ is a substituted aryloxyalkyl group, particularly preferably a branched alkyl group substituted by an aryloxy group similarly to the $R_4$ in Formula C-I. The $X_3$ is a halogen atom, particularly a chlorine atom.

The following are typical examples of the cyan coupler.

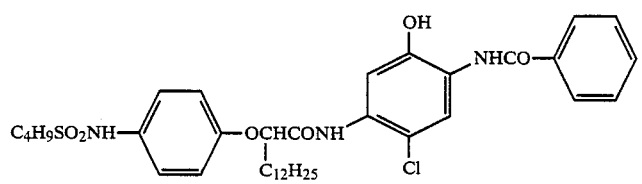

C-1

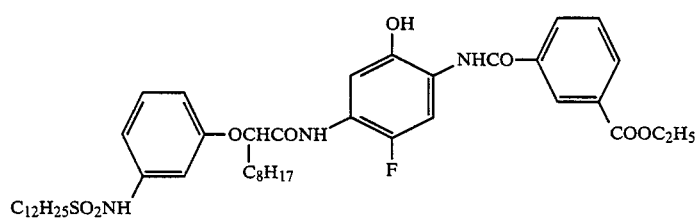

C-2

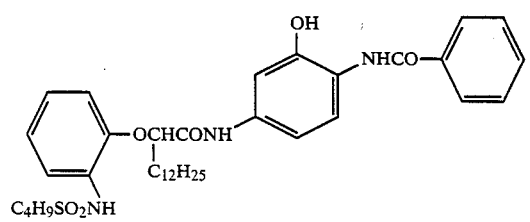

C-3

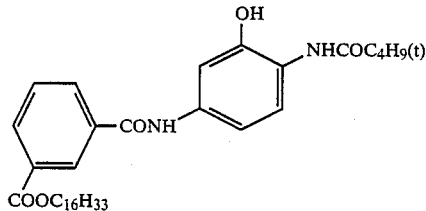
C-4
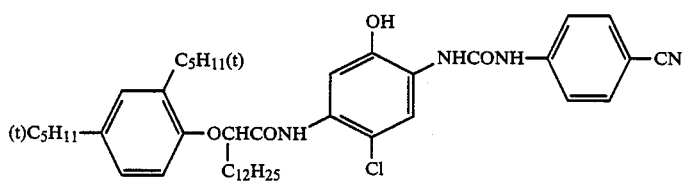
C-5
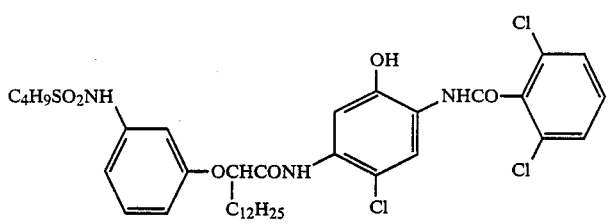
C-6
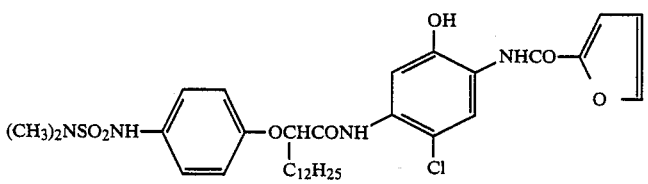
C-7
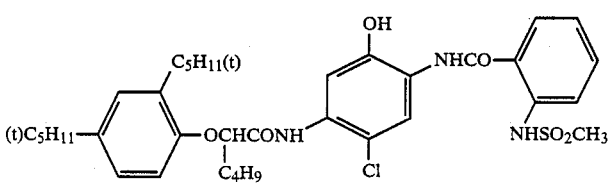
C-8
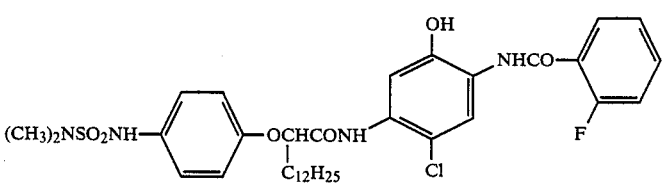
C-9
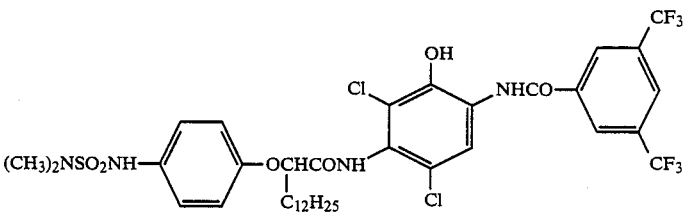
C-10
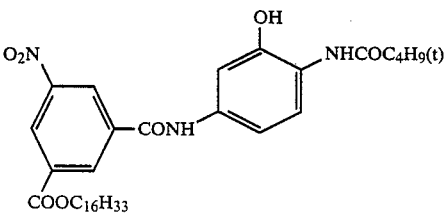
C-11

-continued
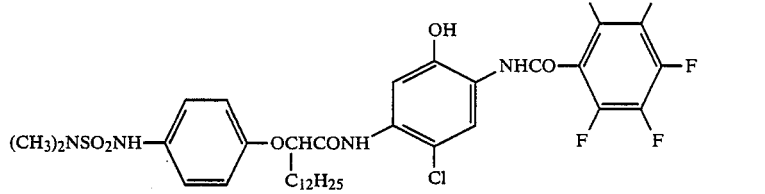
C-12
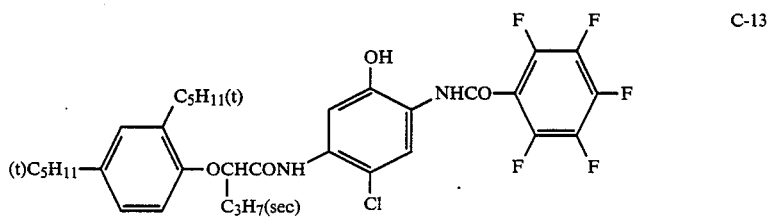
C-13
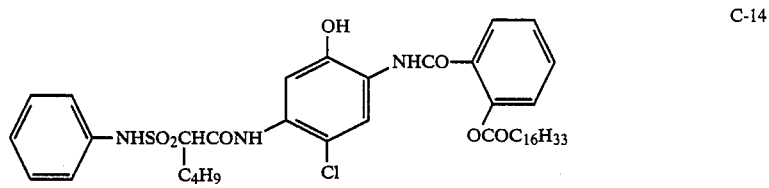
C-14
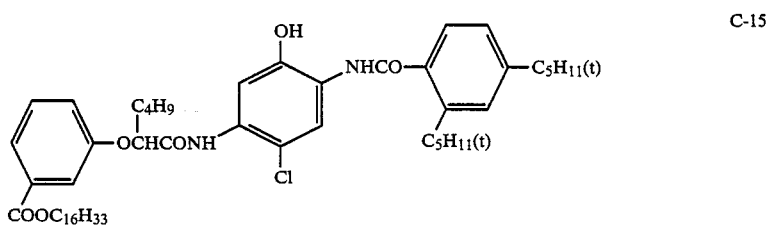
C-15
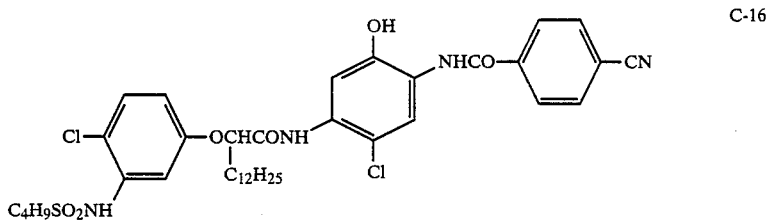
C-16
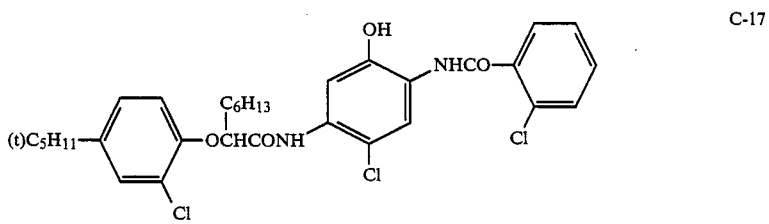
C-17
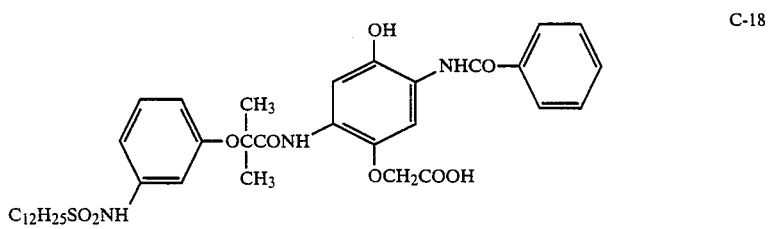
C-18

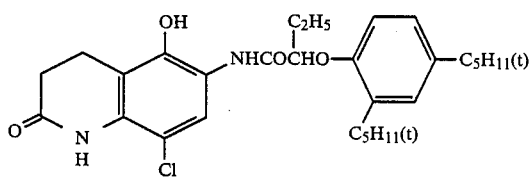
C-19
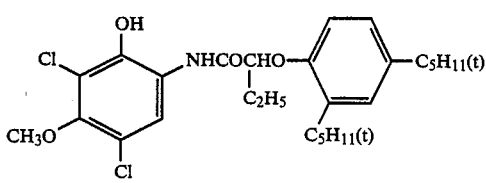
C-20
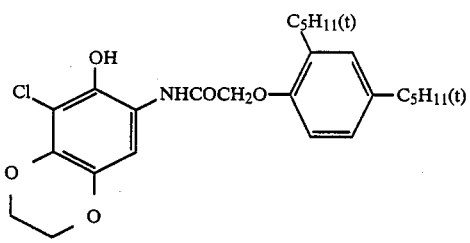
C-21
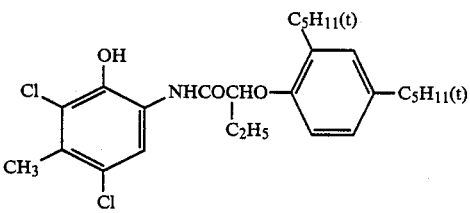
C-22
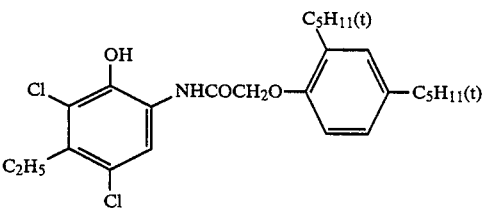
C-23
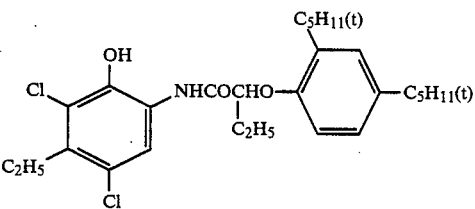
C-24
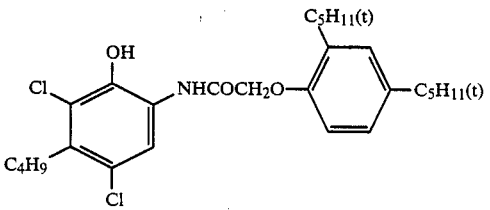
C-25

-continued

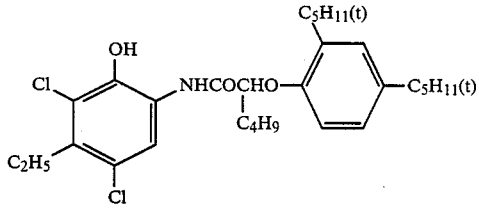
C-26

EXAMPLES

The present invention will be illustrated in detail by the following examples, but the embodiment of the invention is not limited to the examples.

Example 1

One gram each of the magenta couplers of this invention and of the comparative couplers which all are given in Table 1 was taken, and to this were added the same weight of dioctyl phthalate and threefold weight of ethyl acetate, and the temperature that was required for each coupler to be completely dissolved was measured. The results are as shown in Table 1.

TABLE 1

| Test No. | Coupler used | Temperature (°C.) for dissolution |
| --- | --- | --- |
| 1 (Invention) | M-1 | Room temperature |
| 2 (Invention) | M-3 | Room temperature |
| 3 (Invention) | M-5 | Room temperature |
| 4 (Invention) | M-6 | Room temperature |
| 5 (Invention) | M-10 | Room temperature |
| 6 (Invention) | M-11 | Room temperature |
| 7 (Invention) | M-12 | Room temperature |
| 8 (Invention) | M-15 | Room temperature |
| 9 (Invention) | M-16 | Room temperature |
| 10 (Invention) | M-17 | Room temperature |
| 11 (Invention) | M-20 | Room temperature |
| 12 (Invention) | M-29 | Room temperature |
| 13 (Comparative) | Comparative coupler 1* | 50 |
| 14 (Comparative) | Comparative coupler 2* | 60 |

TABLE 1-continued

| Test No. | Coupler used | Temperature (°C.) for dissolution |
|---|---|---|
| 15 (Comparative) | Comparative coupler 3* | 60 |

*Comparative Coupler 1

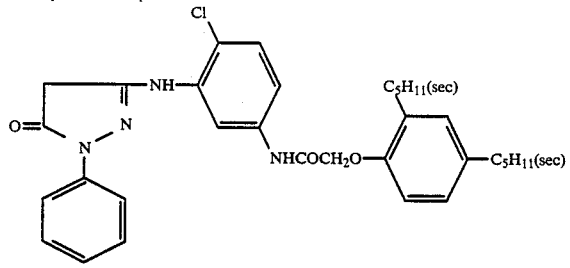

*Comparative Coupler 2

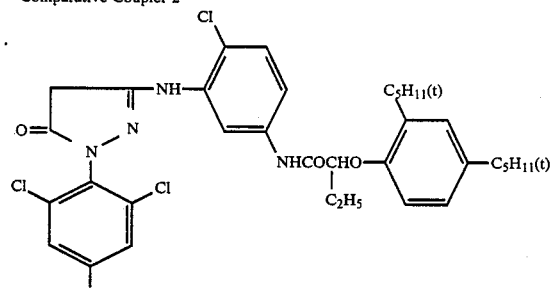

*Comparative Coupler 3

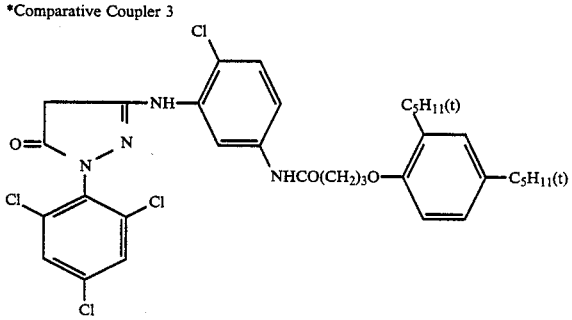

As is apparent from Table 1, these couplers of this invention are excellent in the solubility in organic solvents (high-boiling and low-boiling solvents).

Example 2

The following layers were coated in the described order on a polyethylene resin-coated paper, whereby a color light-sensitive material was prepared. In addition, in the following example, the added amount of each additive to the light-sensitive material is a value per 100 cm².

(1) A layer containing 16 mg of gelatin, 4 mg of a green-sensitive silver chlorobromide emulsion, and 1.9 mg of dioctyl phthalate into which $7 \times 10^{-6}$ mole of Coupler M-1 of this invention and 0.1 mg of 2,5-di-t-octylhydroquinone were dissolved.

(2) A gelatin protective layer containing 9 mg of gelatin.

The thus obtained sample was regarded as Sample 1 for this invention.

On the other hand, Comparative Samples 2, 3, 4 and 5 were prepared in the same manner as in Example 1 except that the Coupler M-1 of this invention was replaced by the following Comparative Couplers 4, 5, 6 and 7, respectively.

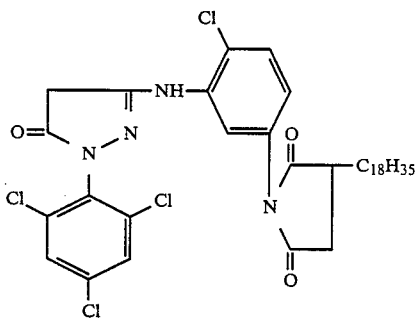

Comparative Coupler 4

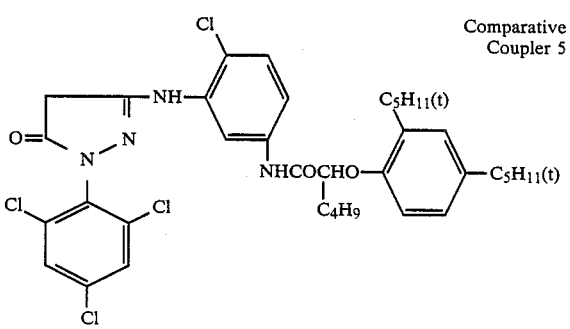

Comparative Coupler 5

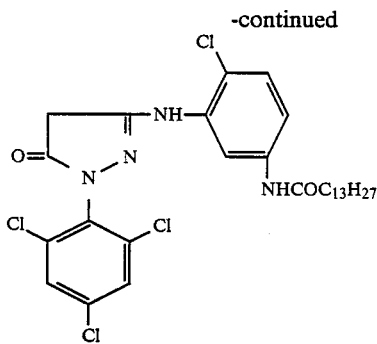

Comparative Coupler 6

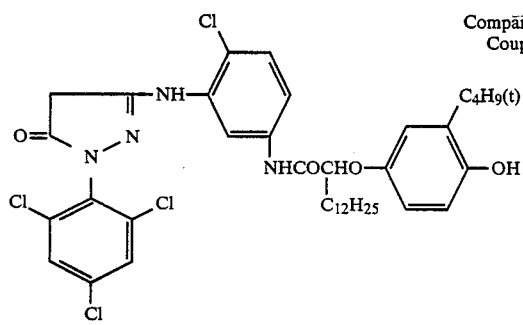

Comparative Coupler 7

Each of Samples 1 through 5 was exposed through an optical wedge in accordance with the sensitometry method, and then processed at 33° C. in the following steps:

| Processing steps | |
| --- | --- |
| Color developing | 3 minutes and 30 seconds |
| Bleach-fix | 1 minute and 30 seconds |
| Washing | 3 minutes |

The compositions of the color developer solution and the bleach-fix bath that were used for processing the samples are as follows:

| Color Developer Solution | |
| --- | --- |
| N—ethyl-N—β-methanesulfonamidoethyl-3-methyl-4-aminoaniline sulfate | 4.9 g |
| Hydroxylamine sulfate | 2.0 g |
| Potassium carbonate | 25.0 g |
| Sodium bromide | 0.6 g |
| Anhydrous sodium sulfite | 2.0 g |
| Benzyl alcohol | 13 ml |
| Polyethylene glycol (average polymerization degree 400) | 3.0 ml |
| Water to make 1 liter. Adjust the pH to 10.0 by using sodium hydroxide. | |
| Bleach-Fix Bath | |
| Ferric-sodium ethylenediaminetetraacetate | 6.0 g |
| Ammonium thiosulfate | 100.0 g |
| Sodium bisulfite | 10.0 g |
| Sodium metabisulfite | 3.0 g |
| Water to make 1 liter. Adjust the pH to 7.0 by using aqueous ammonia. | |

The obtained magenta dye image of each sample was measured with respect to its density by using a Densitometer KD-7R (manufactured by Konica Corporation) to find the sensitivity, fog, maximum density (Dmax), and the maximum absorption wavelength (λmax) at an image density of 1.0 and the half value width at the same density. The sensitivity is expressed in terms of a relative speed to the speed of Sample 1 regarded as 100, and the half value width is a value calculated by the following formula:

$$\text{Half value width} = \lambda_L - \lambda_S$$

wherein $\lambda_L$ is the longer-wavelength-side end wavelength where the image density is 0.5, and $\lambda_S$ is the shorter-wavelength-side end wavelength where the image density is 0.5.

The obtained results are collectively given in Table 2.

TABLE 2

| Sample No. | Coupler used | Speed | Fog | Dmax (nm) | λmax | Half value width (nm) |
| --- | --- | --- | --- | --- | --- | --- |
| 1 (Invention) | M-1 | 100 | 0.03 | 2.52 | 535 | 112 |
| 2 (Comparative) | Comparative-4 | 93 | 0.04 | 2.48 | 529 | 113 |
| 3 (Comparative) | Comparative-5 | 94 | 0.04 | 2.46 | 532 | 113 |
| 4 (Comparative) | Comparative-6 | 92 | 0.03 | 2.40 | 534 | 119 |
| 5 (Comparative) | Comparative-7 | 92 | 0.03 | 2.38 | 536 | 118 |

As is apparent from Table 2, the samples containing Comparative Couplers 6 and 7 show larger half value widths, so that their spectral absorption is broader, while in the ones containing Comparative Couplers 4 and 5, although considerable improvement is seen in their half value widths, their λmax lies a little toward the shorter wavelength side.

In contrast, the sample containing Coupler M-1 of this invention is satisfactory in the λmax as well as in the half value width, thus showing an excellent color reproducibility as the magenta coupler for photographic paper use. In addition, its sensitivity is higher than those of comparative couplers, and thus the coupler of this invention is deemed to be an excellent coupler.

EXAMPLE 3

Samples 6, 7, 8, 9 and 10 were prepared in the same manner as in Example 2 except that Couplers M-5, M-8, M-10, M-12 and M-14 of this invention were used, respectively. Each of these samples was processed in quite the same manner as in Example 2, whereby the results as given in Table 3 were obtained.

TABLE 3

| Sample No. | Coupler used | Speed | Fog | Dmax | λmax (nm) | Half value width (nm) |
| --- | --- | --- | --- | --- | --- | --- |
| 6 (Invention) | M-5 | 105 | 0.03 | 2.52 | 534 | 112 |
| 7 (Invention) | M-8 | 102 | 0.03 | 2.52 | 534 | 111 |
| 8 (Invention) | M-10 | 104 | 0.04 | 2.50 | 533 | 111 |
| 9 (Invention) | M-12 | 102 | 0.03 | 2.50 | 533 | 111 |

TABLE 3-continued

| Sample No. | Coupler used | Speed | Fog | Dmax | λmax (nm) | Half value width (nm) |
|---|---|---|---|---|---|---|
| 10 (Invention) | M-14 | 112 | 0.04 | 2.59 | 534 | 110 |

As is apparent from Table 3, these samples prepared by using the couplers of this invention are all excellent in the color reproducibility as well as in the color formability.

EXAMPLE 4

Preparation of Silver Halide Emulsions:

Six different silver halide emulsions as shown in Table 4 were prepared by the neutral process and simultaneously mixing method.

TABLE 4

| Emulsion No. | AgCl % | AgBr % | Average grain size μm | Chemical sensitizer | Spectral sensitizer |
|---|---|---|---|---|---|
| Em-1 | 99.5 | 0.5 | 0.67 | Sodium thiosulfate*1 | SD-1*3 |
| Em-2 | 99.5 | 0.5 | 0.46 | Chloroauric acid*2 | SD-2*4 |
| Em-3 | 99.5 | 0.5 | 0.43 | | SD-3*5 |
| Em-4 | 10 | 90 | 0.67 | Sodium thiosulfate*1 | SD-1*3 |
| Em-5 | 30 | 70 | 0.46 | | SD-2*4 |
| Em-6 | 30 | 70 | 0.43 | | SD-1*5 |

*1 2 mg per mole of silver halide
*2 5 × 10⁻⁵ mole per mole of silver halide
*3 0.9 millimole per mole of silver halide
*4 0.7 millimole per mole of silver halide
*5 0.2 millimole per mole of silver halide To each silver halide emulsion, after completion of its chemical sensitization, was added $5 \times 10^{-3}$ mole per mole of silver halide of the following Stabilizer STB-1.

Preparation of Silver Halide Light-Sensitive Color Photographic Material Samples:

The following layers were coated in the described order on an anatase-type titanium oxide-containing polyethylene resin-coated paper support, whereby a silver halide lightsensitive color photographic material was prepared.

Layer 1: Layer containing 20 mg of gelatin, 5 mg in silver equivalent of a blue-sensitive silver chlorobromide emulsion Em-1 and 3 mg of dioctyl phthalate as a solvent into which 8 mg of Y-Coupler* and 0.1 mg of 2,5-di-t-octylhydroquinone are dissolved.

Layer 2: Intermediate layer containing 12 mg of gelatin and 2 mg of dibutyl phthalate as a solvent into which 0.5 mg of 2,5-di-t-octylhydroquinone and 4 mg of an ultraviolet absorbing agent* are dissolved.

Layer 3: Layer containing 18 mg of gelatin, 4 mg in silver equivalent of a green-sensitive silver chlorobromide emulsion Em-2 and 2.5 mg of dioctyl phthalate as a coupler solvent into which 5 mg of M-Coupler*, 2 mg of an antioxidation agent* and 0.2 mg of 2,5-di-t-octylhydroquinone are dissolved.

Layer 4: Intermediate layer containing the same components as those of Layer 2.

Layer 5: Layer containing 16 mg of gelatin, 4 mg in silver equivalent of a red-sensitive silver chlorobromide emulsion Em-3 and 2.0 mg of tricresyl phosphate as a solvent into which 3.5 mg of C-Coupler* and 0.1 mg of 2,5-di-t-octylhydroquinone are dissolved.

Layer 6: Protective layer containing 9 mg of gelatin.

A coating aid was added to each of Layers 1 through 6, and further to each of Layers 4 through 6 was added a gelatin bridging agent.

The ultraviolet absorbing agent that was added to

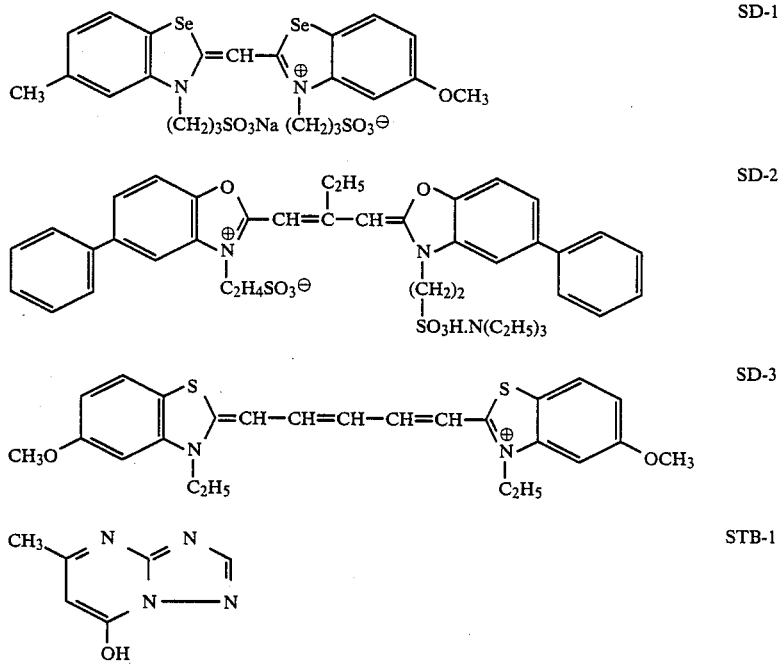

Layers 2 and 4 was a equimolar mixture of U-1 and U-2.

The antioxidation agent that was used in Layer 3 was di-t-pentylhydroquinone-di-octyl ether.

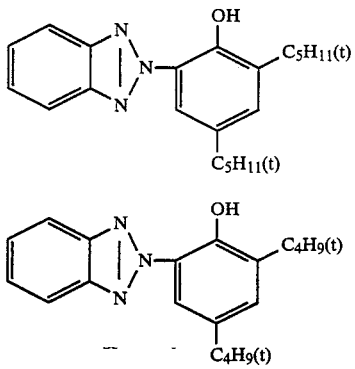

U-1

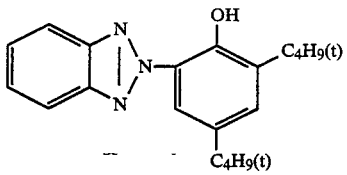

U-2

Each of the obtained samples was exposed through an optical wedge by using a Sensitometer KS-7 (manufactured by Konica Corporation), and then processed in accordance with the following color developing process. After that each of the processed samples was measured with respect to its sensitivity, fog, and the maximum density (Dmax) of the greensensitive emulsion layer by means of an Optical Densitometer PDA-65 (manufactured by Konica Corporation). The sensitivity of each sample is expressed in terms of a relative speed to the speed of Sample 11 regarded as 100. Also, the maximum absorption wavelength $\lambda$max at a magenta dye image density of 1.0 and the half value width at the same density were measured.

Further, each of the obtained samples was exposed over a period of 15 days to the light of a xenon color fastness tester, and after that, the residual rate (%) of the dye image at the initial density point of 1.0 was found, whereby the fastness to light of each sample was evaluated.

The Y-Coupler, M-Coupler and C-Coupler that were used in the respective layers of each sample and the obtained results are collectively shown in Table 5.

| Processing Steps: | | |
| --- | --- | --- |
| Color developing | 34.7 ± 0.3° C. | 45 seconds |
| Bleach-fix | 34.7 ± 0.5° C. | 45 seconds |
| Stabilizing | 30 to 34° C. | 90 seconds |
| Drying | 60 to 80° C. | 60 seconds |
| Color Developer Solution | | |
| Pure water | | 800 ml |
| Triethanolamine | | 8 g |
| N,N-diethylhydroxylamine | | 5 g |
| Potassium chloride | | 2 g |

| -continued | |
| --- | --- |
| N-ethyl-N-$\beta$-methanesulfonamidoethyl-3-methyl-4-aminoaniline sulfate | 5 g |
| Sodium tetrapolyphosphate | 2 g |
| Potassium carbonate | 30 g |
| Potassium sulfite | 0.2 g |
| Brightening agent (4,4'-diaminostilbene-disulfonic acid derivative) | 1 g |
| Pure water to make 1 liter. Adjust the pH to 10.2. | |
| Bleach-Fix Bath | |
| Ferric-ammonium ethylenediaminetetra-acetate, dihydrated | 60 g |
| Ethylenediaminetetraacetic acid | 3 g |
| Ammonium thiosulfate (aqueous 70% solution) | 100 ml |
| Ammonium sulfite (aqueous 40% solution) | 27.5 ml |
| Water to make 1 liter. Adjust the pH to 5.7 by using potassium carbonate or glacial acetic acid. | |
| Stabilizing Bath | |
| 5-Chloro-2-methyl-4-isothiazolin-3-one | 1 g |
| 1-Hydroxyethylidene-1,1-diphosphonic acid | 2 g |
| Water to make 1 liter. Adjust the pH to 7.0 by using sulfuric acid or potassium hydroxide. | |

TABLE 5

| Sample No. | Layer 1 Yellow coupler | Layer 3 Magenta coupler | Layer 5 Cyan coupler | Speed | Fog | Dmax | $\lambda$max (nm) | Half value width (nm) | Dye residual rate (%) |
| --- | --- | --- | --- | --- | --- | --- | --- | --- | --- |
| 11 (Invention) | Y-1 | M-1 | C-12 | 100 | 0.03 | 2.52 | 535 | 112 | 76 |
| 12 (Invention) | Y-5 | " | " | 100 | 0.03 | 2.51 | 535 | 112 | 77 |
| 13 (Invention) | Y-9 | " | " | 100 | 0.03 | 2.52 | 535 | 111 | 77 |
| 14 (Invention) | Y-4 | " | " | 99 | 0.03 | 2.51 | 535 | 112 | 77 |
| 15 (Invention) | Y-25 | " | " | 99 | 0.03 | 2.52 | 535 | 112 | 76 |
| 16 (Invention) | Y-10 | " | C-24 | 100 | 0.03 | 2.52 | 535 | 112 | 77 |
| 17 (Invention) | Y-5 | M-5 | C-12 | 99 | 0.03 | 2.53 | 534 | 111 | 78 |
| 18 (Invention) | Y-9 | " | C-22 | 100 | 0.03 | 2.52 | 534 | 112 | 78 |
| 19 (Invention) | Y-5 | M-15 | C-12 | 100 | 0.04 | 2.53 | 533 | 111 | 78 |
| 20 (Invention) | Y-10 | " | C-22 | 101 | 0.03 | 2.52 | 533 | 110 | 79 |
| 21 (Invention) | " | " | C-24 | 101 | 0.03 | 2.52 | 533 | 110 | 78 |
| 22 (Invention) | " | " | C-12 | 99 | 0.03 | 2.52 | 533 | 111 | 78 |
| 23 (Comparative) | " | Comp-4 | " | 92 | 0.04 | 2.45 | 529 | 113 | 74 |
| 24 (Comparative) | " | Comp-6 | " | 91 | 0.03 | 2.40 | 534 | 119 | 50 |
| 25 (Comparative) | " | Comp-7 | " | 92 | 0.03 | 2.38 | 536 | 118 | 69 |

As is apparent from Table 5, Samples 11 through 22 which contain the magenta couplers of this invention have longer $\lambda$max wavelengths than the $\lambda$max wavelength of Sample 23 containing Comparative Coupler 4, and have smaller half value widths than those of Samples 24 and 25 containing Comparative Couplers 6 and 7, and thus these magenta couplers of this invention show excellent color reproducibility as the magenta coupler for photographic paper. Further, Samples 11 through 22 are excellent in the color formability as well as in the fastness to light as compared to Samples 23, 24 and 25, and thus these magenta couplers of this invention are proved to be significantly excellent.

EXAMPLE 5

Silver halide light-sensitive color photographic material Samples 26 through 40 were prepared in the same manner as in Example 4 except that the blue-sensitive silver halide emulsion of Layer 1 of the silver halide light-sensitive material that was prepared in Example 4 was replaced by the emulsion Em-4 given in Table 4, the green-sensitive silver halide emulsion of Layer 3 was replaced by the emulsion Em-5 given in Table 4, the red-sensitive silver halide emulsion of Layer 5 was replaced by the emulsion Em-6 in Table 4, and into Layer 1, Layer 3 and Layer 5 were incorporated the Y-Coupler, M-Coupler and C-Coupler shown in Table 6, respectively.

Each of the obtained samples was exposed through an optical wedge by using a Sensitometer KS-7 (manufactured by Konica Corporation) and then processed in the same manner as in Example 2. After that, these processed samples were subjected to similar measurements to Example 4.

The obtained results are as given in Table 6.

TABLE 6

| Sample No. | Layer 1 Yellow coupler | Layer 3 Magenta coupler | Layer 5 Cyan coupler | Speed | Fog | Dmax | λmax (nm) | Half value width (nm) | Dye residual rate (%) |
|---|---|---|---|---|---|---|---|---|---|
| 26 (Invention) | Y-6 | M-3 | C-13 | 101 | 0.03 | 2.52 | 535 | 112 | 76 |
| 27 (Invention) | " | " | C-8 | 100 | 0.03 | 2.51 | 535 | 112 | 77 |
| 28 (Invention) | " | " | " | 102 | 0.03 | 2.52 | 534 | 111 | 77 |
| 29 (Invention) | " | " | C-26 | 100 | 0.03 | 2.51 | 535 | 112 | 77 |
| 30 (Invention) | Y-5 | M-6 | C-13 | 100 | 0.03 | 2.52 | 535 | 112 | 78 |
| 31 (Invention) | Y-7 | " | C-8 | 101 | 0.03 | 2.51 | 534 | 111 | 78 |
| 32 (Invention) | Y-8 | M-7 | " | 105 | 0.03 | 2.59 | 535 | 111 | 77 |
| 33 (Invention) | Y-9 | M-12 | C-20 | 100 | 0.03 | 2.51 | 534 | 111 | 78 |
| 34 (Invention) | Y-5 | M-3 | C-26 | 100 | 0.03 | 2.51 | 535 | 112 | 77 |
| 35 (Invention) | " | M-6 | " | 100 | 0.03 | 2.51 | 534 | 111 | 78 |
| 36 (Invention) | " | M-7 | " | 100 | 0.03 | 2.51 | 534 | 111 | 77 |
| 37 (Invention) | " | M-12 | " | 101 | 0.03 | 2.52 | 533 | 111 | 78 |
| 38 (Comparative) | " | Comp-6 | " | 91 | 0.03 | 2.41 | 534 | 119 | 50 |
| 39 (Comparative) | " | Comp-7 | " | 92 | 0.03 | 2.39 | 536 | 118 | 69 |
| 40 (Comparative) | " | Comp-8 | " | 92 | 0.05 | 2.37 | 539 | 118 | 55 |

Comparative Coupler 8

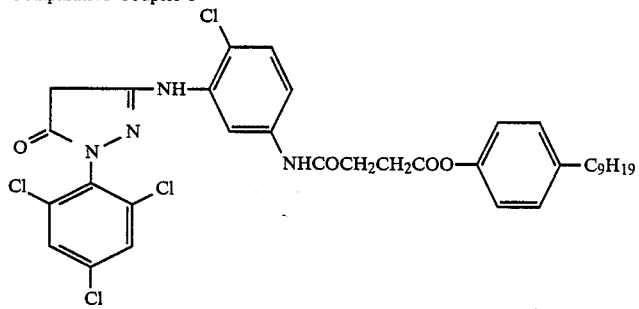

As is apparent from Table 6, Samples 26 through 37 which contain the magenta couplers of this invention have higher sensitivities, smaller half value widths and better light resistance than those of Samples 38, 39 and 40, and thus they are color photographic light-sensitive materials excellent in the fastness to light as well as in the color reproducibility and color formability.

EXAMPLE 6

On a triacetyl cellulose film support were coated the following compositions-having layers in order from the support side, whereby a multicolor light-sensitive material Sample 41 was prepared. The following added amount of each additive to the silver halide light-sensitive material is a value per m² unless otherwise stated. The amount of each of the silver halide and colloidal silver is in silver equivalent.

Layer 1: Antihalation layer

A gelatin layer containing black colloidal silver.

Layer 2: Intermediate layer

A gelatin layer containing an emulsifiedly dispersed product of 2,5-di-t-octylhydroquinone.

Layer 3: Low-speed red-sensitive silver halide emulsion layer

A layer of a monodisperse emulsion Em-7 comprising AgBrI containing 6 mole % AgI, having an average grain diameter of 0.30 μm. The coatin weight of silver is 1.8 g/m². The emulsion layer also contains:

Sensitizing Dye I ... $6 \times 10^{-5}$ mole per mole of silver

Sensitizing Dye II ... $1.0 \times 10^{-5}$ mole per mole of silver

Cyan Coupler C'-1 ... 0.06 mole per mole of silver

Colored Cyan Coupler CC-1 ... 0.003 mole per mole of silver

DIR Compound D-1 ... 0.0015 mole per mole of silver

DIR Compound D-2 ... 0.002 mole per mole of silver

Layer 4: High-speed red-sensitive silver halide emulsion layer

A layer of a monodisperse emulsion Em-8 comprising AgBrI containing 7.0 mole % AgI, having an average grain diameter of 0.5 μm. The coating weight of silver is 1.3 g/m². The emulsion layer also contains:

Sensitizing Dye I ... $3 \times 10^{-5}$ mole of silver

Sensitizing Dye II ... $1.0 \times 10^{-5}$ mole per mole of silver

Cyan Coupler C'-1 ... 0.02 mole per mole of silver

Colored Cyan Coupler CC-1 ... 0.0015 mole per mole of silver

DIR Compound D-2 .... 0.001 mole per mole of silver

Layer 5: Intermediate layer

A gelatin layer of the same composition as Layer 2.

Layer 6: Low-speed green-sensitive silver halide emulsion layer

An emulsion layer containing:

Emulsion Em-7 ... coating weight of silver: 1.5 g/m²

Sensitizing Dye III ... $2.5 \times 10^{-5}$ mole per mole of silver

Sensitizing Dye IV ... $1.2 \times 10^{-5}$ mole per mole of silver

Magenta Coupler M'-1 ... 0.050 mole per mole of silver

Colored Magenta Coupler CM-1 . . . 0.009 mole per mole of silver

DIR Compound D-1 . . . 0.0010 mole per mole of silver

DIR Compound D-3 . . . 0.0030 mole per mole of silver

Layer 7: High-speed green-sensitive silver halide emulsion layer

An emulsion layer containing:

Emulsion Em-8 . . . coating weight of silver: 1.4 g/m²

Sensitizing Dye III . . . $1.5 \times 10^{-5}$ mole per mole of silver

Sensitizing Dye IV . . . $1.0 \times 10^{-5}$ mole per mole of silver

Magenta Coupler M'-1 . . . 0.020 mole per mole of silver

Colored Magenta Coupler CM-1 . . . 0.002 mole per mole of silver

DIR Compound D-3 . . . 0.0010 mole per mole of silver

Layer 8: Yellow filter layer

A gelatin layer containing an emulsifiedly dispersed product of yellow colloidal silver and 2,5-di-t-octylhydroquinone.

Layer 9: Low-speed blue-sensitive silver halide emulsion layer

A layer of a monodisperse emulsion Em-9 comprising AgBrI containing 6.0 mole % AgI, having an average grain diameter of 0.48 μm. The coatin weight of silver is 0.9 g/m². The emulsion layer also contains:

Sensitizing Dye V . . . $1.3 \times 10^{-5}$ mole per mole of silver

Yellow Coupler Y'-1 . . . 0.29 mole per mole of silver

Layer 10: High-speed blue-sensitive silver halide emulsion layer

An layer of a monodisperse emulsion Em-10 comprising AgBrI containing 15 mole% AgI, having an average grain diameter of 0.8 μm. The coating weight of silver: 0.5 g/m². The emulsion layer also contains:

Sensitizing Dye V . . . $1.0 \times 10^{-5}$ mole per mole of silver

Yellow Coupler Y'-1 . . . 0.08 mole per mole of silver

DIR Compound D-2 . . . 0.0015 mole per mole of silver

Layer 11: First protective layer

A gelatin layer containing silver iodobromide grains (1 mole % AgI, average grain diameter 0.7 μm) and a mixture of Ultraviolet Absorbing Agents UV-1 and UV-2 (mixing ration: 1:1).

Layer 12: Second protective layer

A layer containing polymethyl methacrylate particles (average particle size 1.5 μm) and Formaline Scavenger HS-1.

In addition, to these layers were added Gelatin Hardener H-1 and a surface active agent besides the above compositions.

Further, Samples 42 through 49 were prepared in the same manner as in Sample 41 except that the M'-1 in Layers 6 and 7 of Sample 41 was replaced by those couplers given in Table 7.

The compound contained in the above-mentioned layers are as follows:

Sensitizing Dye I: Anhydro-5,5'-dichloro-9-ethyl-3,3'-di-(3-sulfopropyl)thiacarbocyanine-hydroxide Sensitizing Dye II: Anhydro-9-ethyl-3,3'-di-(3-sulfopropyl)4,5,4',5'-dibenzothiacarbocyanine-hydroxide Sensitizing Dye III: Anhydro-5,5'-diphenyl-9-ethyl-3,3+-di-(3sulfopropyl)oxacarbocyanine-hydroxide Sensitizing Dye IV: Anhydro-9-ethyl-3,3'-di-(3-sulfopropyl)5,6,5',6'-dibenzoxacarbocyanine-hydroxide Sensitizing Dye V: Anhydro-3,3'-di-(3-sulfopropyl)-4,5-benzo5'-methoxythiacyanine-hydroxide

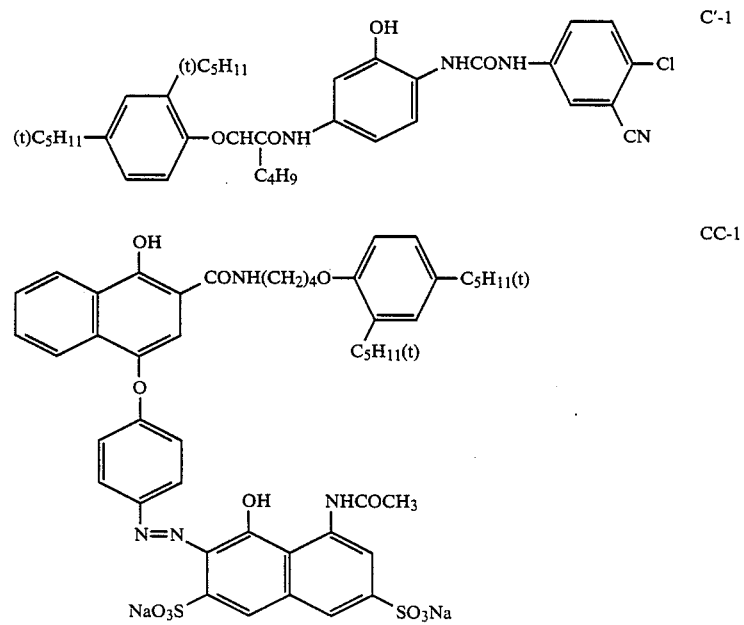

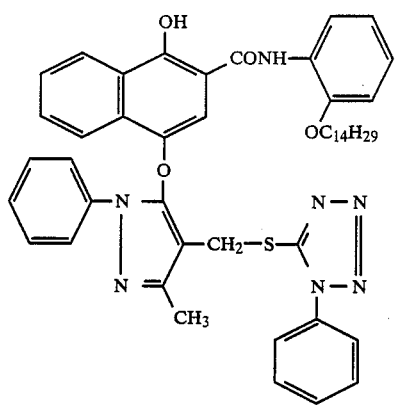
D-1
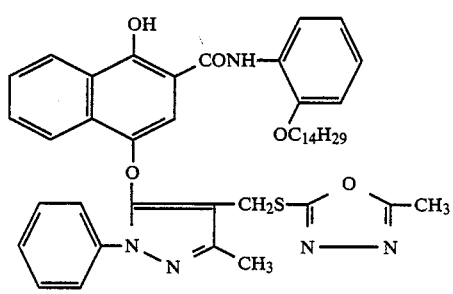
D-2
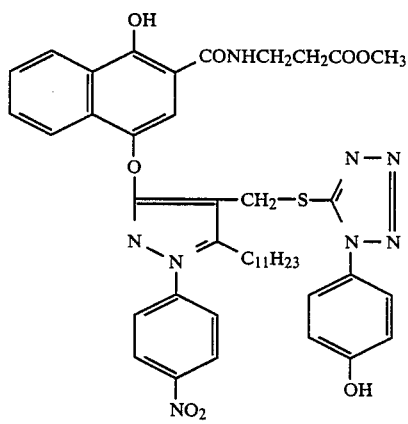
D-3
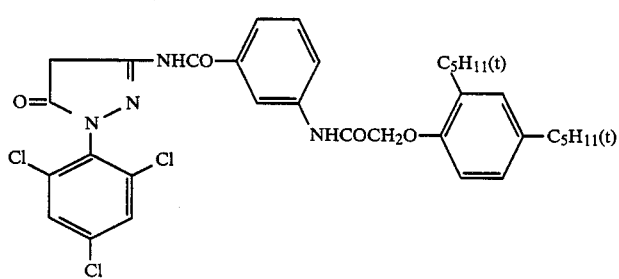
M'-1

CM-1

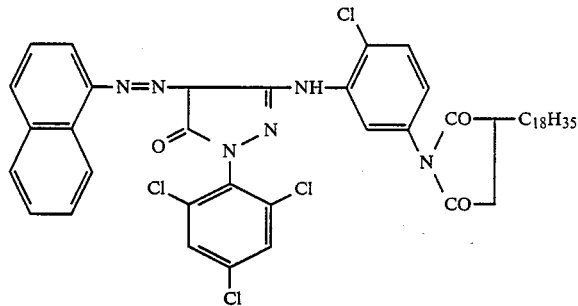

Y-1

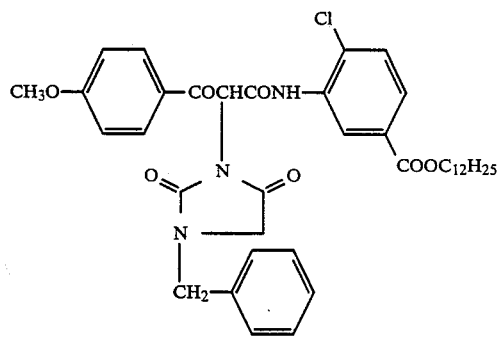

UV-1

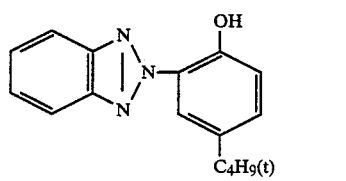

UV-2

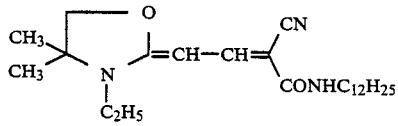

HS-1

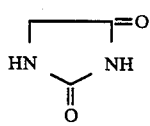

H-1

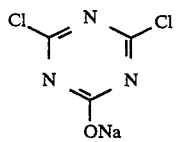

Each of the obtained Samples 41 through 49 was exposed through an optical wedge to a white light, and then processed in accordance with the following steps:

| Processing Steps (38° C.) | |
|---|---|
| Color developing | 3 minutes and 15 seconds |
| Bleaching | 6 minutes and 30 seconds |
| Washing | 3 minutes and 15 seconds |
| Fixing | 6 minutes and 30 seconds |
| Washing | 3 minutes and 15 seconds |
| Stabilizing | 1 minute and 30 seconds |
| Drying | |

The compositions of the processing solutions that were used in the respective processing steps are as follows:

| Color Developer Solutions | |
|---|---|
| 4-Amino-3-methyl-N-ethyl-N-(β-hydroxyethyl)-aniline sulfate | 4.75 g |
| Anhydrous sodium sulfite | 4.25 g |
| Hydroxylamine ½ sulfate | 2.0 g |
| Anhydrous potassium carbonate | 37.5 g |
| Sodium bromide | 1.3 g |
| Trisodium nitrilotriacetate, monohydrated | 2.5 g |
| Potassium hydroxide | 1.0 g |
| Water to make 1 liter | |
| Bleaching Bath | |
| Ferric-ammonium ethylenediaminetetraacetate | 100.0 g |
| Diammonium ethylenediaminetetraacetate | 10.0 g |

-continued

| | |
|---|---|
| Ammonium bromide | 150.0 g |
| Glacial acetic acid | 10.0 ml |
| Water to make 1 liter. Adjust the pH to 6.0 by using aqueous ammonia. | |

Fixer Bath

| | |
|---|---|
| Ammonium thiosulfate | 175.0 g |
| Anhydrous sodium sulfite | 8.5 g |
| Sodium metabisulfite | 2.3 g |
| Water to make 1 liter. Adjust the pH to 6.0 by using acetic acid. | |

Stabilizing Bath

| | |
|---|---|
| Formalin (aqueous 37% solution) | 1.5 ml |
| Koniducks (product of Konica Corporation) | 7.5 ml |
| Water to make 1 liter | |

The magenta dye image obtained by processing each sample was measured with respect to its density by using a densitometer to find its sensitivity and maximum density (Dmax).

The obtained results are given in Table 7. The sensitivity of each sample is a relative speed to the speed of Sample 41 regarded as 100.

TABLE 7

| Sample No. | Coupler used | Sensitivity | Dmax |
|---|---|---|---|
| 41 (Comparative) | M'-1 | 100 | 2.10 |
| 42 (Invention) | M-16 | 110 | 2.50 |
| 43 (Invention) | M-17 | 111 | 2.51 |
| 44 (Invention) | M-18 | 112 | 2.51 |
| 45 (Invention) | M-20 | 114 | 2.53 |
| 46 (Invention) | M-21 | 114 | 2.52 |
| 47 (Invention) | M-22 | 113 | 2.53 |
| 48 (Invention) | M-27 | 113 | 2.52 |
| 49 (Invention) | M-28 | 112 | 2.52 |

As is apparent from Table 7, any of these samples of this invention show high Dmax values, so that the couplers of this invention are excellent in the color formability.

EXAMPLE 7

Color light-sensitive material Samples 50 through 56 were prepared in the same manner as in Example 6 except that those couplers as given in Table 8 were used in place of the magenta couplers in Example 6.

Each of the obtained samples was processed in the same manner as in Example 6, and the obtained magenta dye image was measured with respect to its density to find its sensitivity and maximum density (Dmax).

The obtained results are as given in Table 8. In the table, the sensitivity of each sample is a relative speed to the speed of Sample 50 regarded as 100.

TABLE 8

| Sample No. | Coupler used | Sensitivity | Dmax |
|---|---|---|---|
| 50 (Comparative) | M'-2 | 100 | 2.50 |
| 51 (Invention) | M-19 | 110 | 2.60 |
| 52 (Invention) | M-23 | 111 | 2.61 |
| 53 (Invention) | M-24 | 112 | 2.60 |
| 54 (Invention) | M-26 | 114 | 2.61 |
| 55 (Invention) | M-29 | 112 | 2.60 |
| 56 (Invention) | M-32 | 113 | 2.60 |

Comparative Coupler M'-2

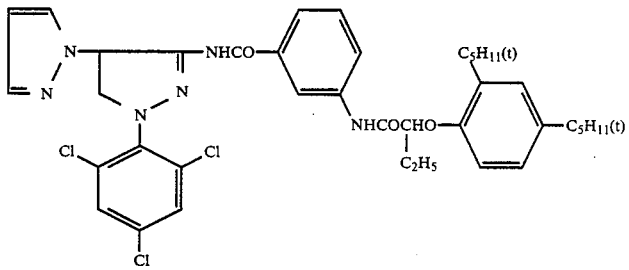

As is apparent from Table 8, any of the samples containing these magenta couplers of this invention show high sensitivities and Dmax values as compared to the sample containing the comparative coupler, so that they are excellent color light-sensitive materials.

What is claimed is:

1. A silver halide color photographic light-sensitive material comprising a support having thereon at least one silver halide emulsion layer containing a magenta coupler represented by the following Formula M-1;

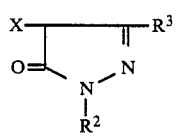

Formula M-I wherein $R^2$ and $R^3$ are each a substituent, provided that at least one of which has a group represented by the following Formula I; and X is a hydrogen atom or a group capable of being split off upon reaction with the oxidation product of a color developing agent,

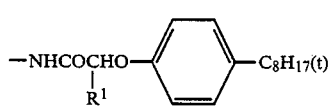

Formula I wherein $R^1$ is a hydrogen atom or a normal or branched alkyl group having 1 to 20 carbon atoms.

2. The material of claim 1, wherein said $R^2$ is a substituted or unsubstituted aryl group.

3. The material of claim 2, said $R^2$ is a substituted aryl group.

4. The material of claim 3, wherein a substituent contained in said substituted aryl group is a halogen atom, an alkyl group, an alkoxy group, an aryloxy group, an acylamino group, a sulfonylamino group, a sulfamoyl group, a carbamoyl group, a sulfonyl group, an acyloxy group, an ester group, a carboxy group, a sulfo group, a cyano group or a nitro group.

5. The material of claim 1, wherein said $R^3$ is a substituted or unsubstituted anilino group, a substituted or unsubstituted acylamino group, a substituted or unsubstituted ureido group or a substituted or unsubstituted carbamoyl group.

6. The material of claim 1, wherein said $R^1$ is a hydrogen atom or an alkyl group having 1 to 12 carbon atoms.

7. The material of claim 1, wherein said magenta coupler is contained in said silver halide emulsion layer in an amount of from $7\times10^{-2}$ mol to $7\times10^{-1}$ mol per mol of silver halide contained in said emulsion layer.

8. The material of claim 7, wherein said magenta coupler is contained in said silver halide emulsion layer in an amount of from $1\times10^{-1}$ mol to $4\times10^{-1}$ mol per mol of silver halide contained in said emulsion layer.

* * * * *